(12) United States Patent
Harish et al.

(10) Patent No.: US 6,506,437 B1
(45) Date of Patent: Jan. 14, 2003

(54) METHODS OF COATING AN IMPLANTABLE DEVICE HAVING DEPOTS FORMED IN A SURFACE THEREOF

(75) Inventors: Sameer Harish, Fremont, CA (US); Steven Z. Wu, Santa Clara, CA (US); Kurt W. Scheinpflug, Santa Clara, CA (US); Brandon Yoe, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 54 days.

(21) Appl. No.: 09/690,907

(22) Filed: Oct. 17, 2000

(51) Int. Cl.$^7$ .................................................. B05D 3/00
(52) U.S. Cl. .................... 427/2.25; 623/1.34; 623/1.39; 623/1.42
(58) Field of Search ................ 623/1.15, 1.34, 623/1.39, 1.42, 1.43, 1.45, 1.46; 427/2.14, 2.24, 2.25, 2.28, 2.1

(56) References Cited

U.S. PATENT DOCUMENTS

| | | | |
|---|---|---|---|
| 3,987,219 A | 10/1976 | Arvidsson | 427/297 |
| 4,459,252 A | 7/1984 | MacGregor | 264/46.9 |
| 4,532,277 A * | 7/1985 | Wingler | 351/160 R |
| 4,552,781 A | 11/1985 | Cannady, Jr. et al. | 427/57 |
| 4,733,665 A | 3/1988 | Palmaz | 128/343 |

(List continued on next page.)

FOREIGN PATENT DOCUMENTS

| | | | | |
|---|---|---|---|---|
| EP | 0850651 | 7/1998 | | |
| EP | 0875218 | 11/1998 | | |
| JP | 11299901 | 11/1999 | | |
| WO | 90/01969 | 3/1990 | | |
| WO | WO 98/ 23228 | 6/1998 | ............. | A61F/2/06 |
| WO | 99/16386 | 4/1999 | | |

Primary Examiner—Paul B. Prebilic
Assistant Examiner—William H Matthews
(74) Attorney, Agent, or Firm—Squire Sanders & Dempsey L.L.P.

(57) ABSTRACT

The present invention provides methods of coating an implantable device, such as a stent or a graft, having a plurality of depots formed in a surface thereof. An exemplary method includes applying a composition including a polymer and a solvent to the implantable device proximate to the depots. Such application of the composition is performed at a first gas pressure. The method also includes applying a second gas pressure, which is greater than the first gas pressure, to the composition-coated device so that air pockets in the depots are eliminated, or at least reduced in size. The method also includes the act of removing the solvent from the composition to form a coating. An implantable device coated in accordance with the method is also provided.

The compositions employed in the methods may include one or more therapeutic substances such as antineoplastics, antimitotics, antiinflammatories, antiplatelets, anticoagulants, antifibrins, antithrombins, antiproliferatives, antibiotics, antioxidants, antiallergics, radioisotopes, and combinations thereof.

32 Claims, 6 Drawing Sheets

U.S. PATENT DOCUMENTS

| | | | |
|---|---|---|---|
| 4,800,882 A | | 1/1989 | Gianturco ................... 128/343 |
| 4,806,595 A | * | 2/1989 | Noishiki et al. .............. 514/56 |
| 4,886,062 A | | 12/1989 | Wiktor ....................... 128/343 |
| 5,037,377 A | * | 8/1991 | Alonso ................. 128/DIG. 8 |
| 5,059,211 A | | 10/1991 | Stack et al. ................. 606/198 |
| 5,071,674 A | | 12/1991 | Nogues et al. ................ 427/57 |
| 5,163,952 A | | 11/1992 | Froix ............................ 623/1 |
| 5,306,286 A | | 4/1994 | Stack et al. ................. 606/198 |
| 5,340,614 A | * | 8/1994 | Perman et al. ............ 427/2.24 |
| 5,464,650 A | | 11/1995 | Berg et al. .................. 427/2.3 |
| 5,527,337 A | | 6/1996 | Stack et al. ................. 606/198 |
| 5,697,980 A | * | 12/1997 | Otani et al. ................ 424/423 |
| 5,700,286 A | | 12/1997 | Tartaglia ....................... 623/1 |
| 5,713,949 A | | 2/1998 | Jayaraman .................... 623/1 |
| 5,766,710 A | | 6/1998 | Turnlund et al. .......... 428/36.1 |
| 5,769,883 A | | 6/1998 | Buscemi et al. ................ 623/1 |
| 5,817,328 A | * | 10/1998 | Gresser et al. .............. 424/426 |
| 5,843,172 A | | 12/1998 | Yan ............................... 623/1 |
| 5,873,904 A | | 2/1999 | Ragheb et al. .................. 623/1 |
| 5,993,374 A | * | 11/1999 | Kick .............................. 600/8 |
| 6,120,536 A | | 9/2000 | Ding et al. ................. 623/1.43 |
| 6,120,847 A | | 9/2000 | Yang et al. ................. 427/335 |
| 6,149,681 A | | 11/2000 | Houser et al. ............. 623/1.12 |
| 6,206,915 B1 | | 3/2001 | Fagan et al. ............... 623/1.42 |
| 6,253,443 B1 | * | 7/2001 | Johnson ................ 219/121.72 |
| 6,254,632 B1 | * | 7/2001 | Wu et al. ................... 623/1.15 |
| 6,273,908 B1 | * | 8/2001 | Ndondo-Lay .............. 606/194 |
| 6,287,628 B1 | | 9/2001 | Hossainy et al. ............ 427/2.3 |
| 6,306,165 B1 | * | 10/2001 | Patnaik et al. ............. 427/2.25 |
| 6,379,381 B1 | | 4/2002 | Hossainy et al. .......... 623/1.42 |

\* cited by examiner

METHODS OF COATING AN IMPLANTABLE DEVICE HAVING DEPOTS FORMED IN A SURFACE THEREOF

BACKGROUND OF THE INVENTION

1. Field of the Invention

The present invention relates generally to implantable devices, examples of which include stents and grafts. More particularly, the present invention is directed to a method of coating an implantable device having a plurality of depots formed in a surface thereof.

2. Description of the Related Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion against the inner wall of the artery to dilate the lumen. The balloon is then deflated to a smaller profile to allow the catheter to be withdrawn from the patient's vasculature.

A problem associated with the above procedure includes formation of intimal flaps or torn arterial linings which can collapse and occlude the vessel after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, an implantable device, examples of which include stents and grafts, may be implanted.

Stents are scaffoldings, usually cylindrical or tubular in shape, which function to physically hold open and, if desired, to expand the wall of the vessel. Typically stents are capable of being compressed, so that they may be inserted through small cavities via catheters, and then expanded to a larger diameter once they are at the desired location. Examples in patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

Synthetic vascular grafts are vessel-like configurations that may be positioned into the host blood vessel as a replacement for a diseased or occluded segment that has been removed. Alternatively, a graft may be sutured to the host vessel at each end so as to form a bypass conduit around a diseased or occluded segment of the host vessel.

Although stents and grafts are significant innovations in the treatment of occluded vessels, there remains a need for administering therapeutic substances to the treatment site. Systemic administration of the therapeutic substance often produces adverse or toxic side effects for the patient. Local delivery of therapeutic substances, by contrast, provides a smaller overall dosage that is concentrated at a specific site. Local delivery can produce fewer side effects and achieve more effective results in many cases.

One technique for the local delivery of therapeutic substances employs medicated coatings on implantable devices. A typical method for medicating an implantable device includes applying a composition containing a polymer, a solvent, and a therapeutic substance to the implantable device using conventional techniques, such as spray-coating or dip-coating. The method further includes removing the solvent, leaving on the implantable device surface a coating of the polymer with the therapeutic substance impregnated in the polymer.

A recently developed type of stent includes a plurality of pores, called "depots" herein, that are formed in the outer surface of the stent. When such stents are coated using conventional methods, undesirable pockets of air can become trapped in the depots. Accordingly, a new coating method is needed for implantable devices having such depots.

SUMMARY OF THE INVENTION

The present invention provides methods by which implantable devices, such as stents and grafts, having a plurality of depots formed in a first surface thereof may be coated with therapeutic substances, among other possibilities.

An exemplary method within the present invention includes applying a composition including a polymer and a solvent to the first surface of the implantable device proximate to the depots. The application of the composition is performed at a first gas pressure. The method further includes applying a second gas pressure to the implantable device, wherein the second gas pressure is greater than the first gas pressure. Applying such an increased gas pressure drives the composition into the depots and eliminates, or at least reduces the size of, air pockets within the depots. The method also includes removing the solvent from the composition on the implantable device so that a stable, polymer-based coating is formed on the first surface and within the depots of the implantable device.

In some embodiments, the composition additionally includes a therapeutic substance. The therapeutic substance may be selected from antineoplastic, antimitotic, antiinflammatory, antiplatelet, anticoagulant, antifibrin, antithrombin, antiproliferative, antibiotic, antioxidant, and antiallergic substances and combinations thereof. Alternatively, the therapeutic substance may be a radioactive isotope or a radiopaque substance.

These and other aspects of the present invention may be better appreciated in view of the detailed description and drawings of the exemplary embodiments.

DETAILED DESCRIPTION

The present invention provides methods of applying a coating to an implantable device, i.e., a device that is designed to be implanted in a human or animal body, where the implantable device has depots formed in the outer surface thereof. The coating so applied may be polymer-based and may include any therapeutic substance. The present invention provides both effective and economical means for preparing implantable devices that have the capability of delivering therapeutic substances.

Figure 1:
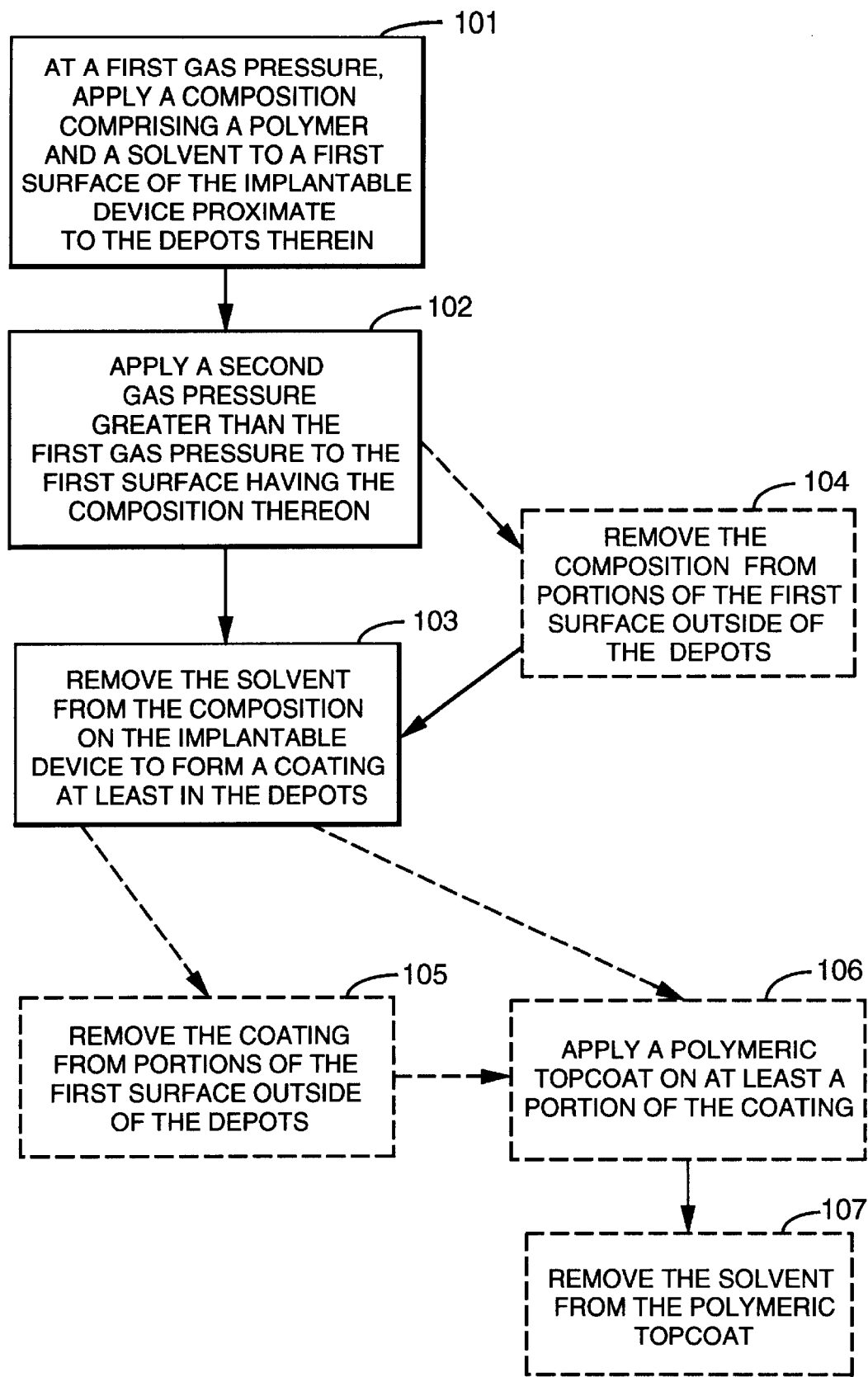
FIG. 1 is a flowchart illustrating exemplary methods of coating an implantable device having depots formed in a surface thereof.

FIG. 1 illustrates a method 100 of coating an implantable device having depots formed in a surface thereof. In act 101 of method 100, a composition including a polymer and a solvent is applied to a first surface of the implantable device. Act 101 is performed at a first gas pressure. The composition may further include a therapeutic substance. In act 102, a second gas pressure is applied to the composition-coated implantable device, wherein the second gas pressure is greater than the first gas pressure at which act 101 is performed. The increased gas pressure forces pockets of air out of the depots. The solvent is removed from the composition on the implantable device in act 103 to form a coating. The composition or the coating may be removed from portions of the implantable device outside of the depots in acts 104 and 105, respectively, thereby yielding an implantable device having a coating solely within the depots. In addition, a polymeric topcoat containing a solvent may be applied on at least a portion of the coating in act 106. The solvent is removed from the topcoat in act 107.

Implantable Device

The implantable device used in conjunction with the present invention may be any implantable device, examples of which include self-expandable stents, balloon-expandable stents, and grafts, among other possibilities. The implantable device can be made of a metallic material or an alloy such as, but not limited to, stainless steel, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The implantable device may also be made from bioabsorbable or biostable polymers. A polymeric implantable device should be chemically compatible with any substance to be loaded onto the implantable device.

Figure 2A:
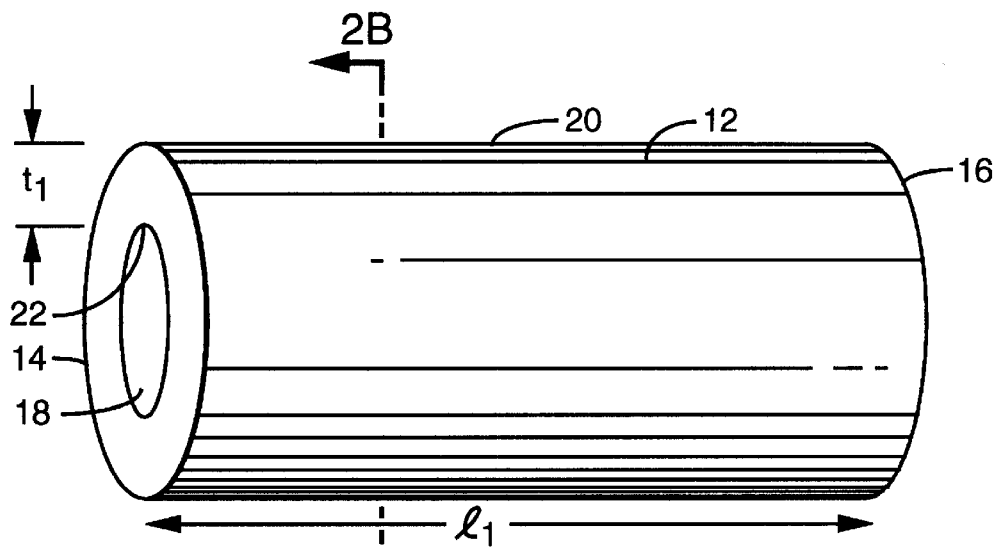
FIG. 2A is a perspective view of an implantable device with a central hollow bore.
Figure 2B:
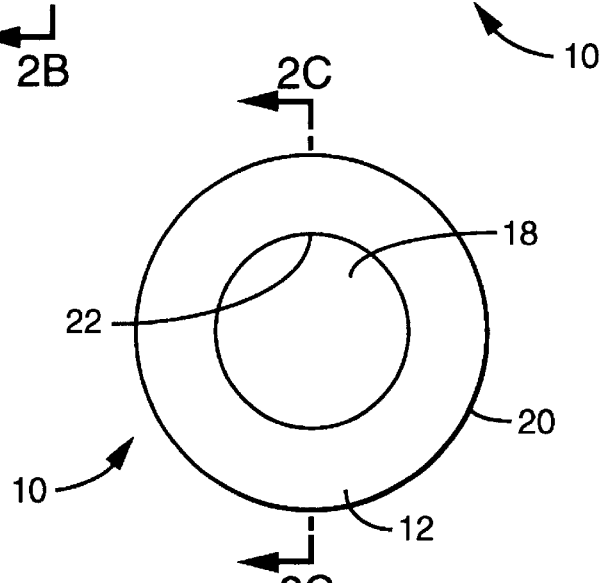
FIG. 2B is a cross-sectional side view of the implantable device of FIG. 2A taken along line 2B—2B of FIG. 2A.
Figure 2C:
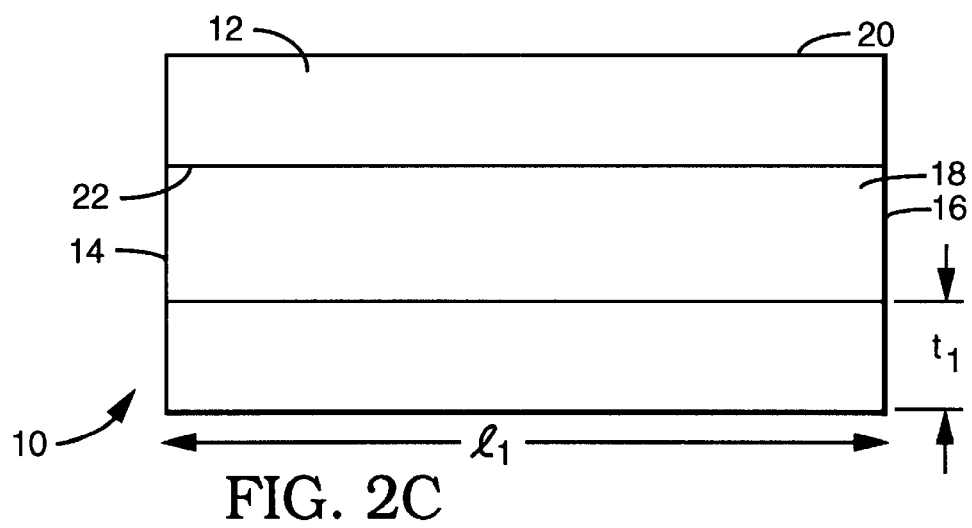
FIG. 2C is a side view of the implantable device of FIG. 2B taken along line 2C—2C of FIG. 2B.

FIGS. 2A, 2B, and 2C provide views of an exemplary implantable device 10, e.g., a stent or graft. Implantable device 10 is a generally tubular structure that includes a body 12 having a first end 14 and an opposing second end 16. A central hollow bore 18 extends longitudinally through body 12 from first end 14 to second end 16, giving body 12 a thickness $t_1$ between an outer surface 20 and an inner surface 22. Implantable device 10 can have any suitable length $l_1$. The values of length $l_1$ and thickness $t_1$, depend, for example, on the procedure for which implantable device 10 is used.

The surface properties of implantable device 10 may vary according to the desired use of implantable device 10. In some embodiments, inner surface 22 and/or outer surface 20 of implantable device 10 is polished using conventional electropolishing methods, abrasive slurry methods, or other polishing methods known to those of ordinary skill in the art. In other embodiments, portions of outer surface 20 are roughened by the creation of asperities while inner surface 22 remains smooth. Asperities can be created by projecting a stream of pressurized grit onto outer surface 20. Asperities can also be formed by removing material from outer surface 20, for example, by chemical etching with or without a patterned mask. Alternatively, asperities can be formed by adding material to outer surface 20, for example, by welding powder to outer surface 20 or by sputtering onto outer surface 20.

Figure 3A:
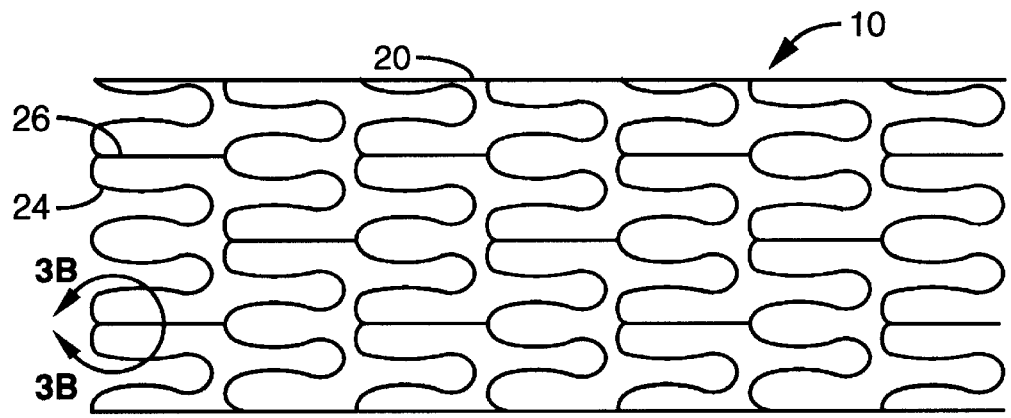
FIG. 3A is a side view of an exemplary stent formed of thread elements engaged to one another by connecting elements.

FIG. 3A is a side view of a stent, which is an exemplary type of implantable device 10. In FIG. 3A, body 12 is formed from a plurality of struts 24 each having arms 25 and a link 26. Arms 25 of neighboring struts 24 are engaged to one another by links 26. However, the underlying structure of implantable device 10 can be of virtually any design.

Figure 3B:
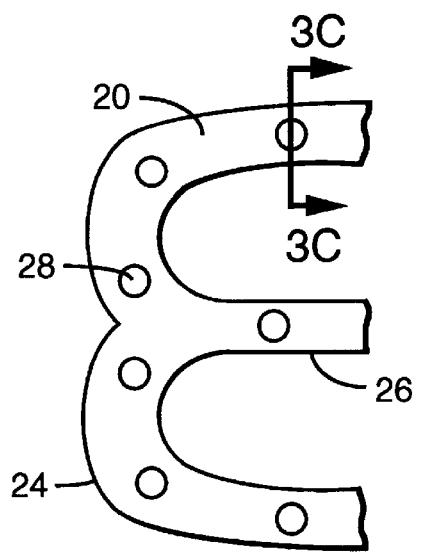
FIG. 3B is an enlarged view of section 3B of the stent of FIG. 3A, wherein the thread elements and connecting elements have depots formed therein.

FIG. 3B illustrates the portion of the exemplary implantable device 10 shown in circle 3B of FIG. 3A. FIG. 3B shows that arms 25 and link 26 of strut 24 have a plurality of depots 28 formed in outer surface 20. Depots 28, which may also be referred to as pores or cavities, can be formed in virtually any implantable device 10 structure at any preselected location within implantable device 10. The location of depots 28 within implantable device 10 varies according to intended usage and application. Depots 28 may be formed on implantable device 10 by exposing outer surface 20 to an energy discharge from a laser, such as, but not limited to, an excimer laser. Alternative methods of forming such depots 28 include, but are not limited to, physical and chemical etching techniques. Such techniques are well-known to one of ordinary skill in the art.

Figure 3C:
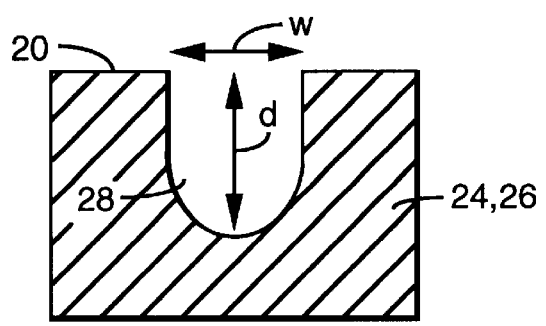
FIG. 3C is a cross-sectional view of a depot within the stent of FIG. 3B taken along line 3C—3C of FIG. 3B.

FIG. 3C is a cross-sectional view of a single depot 28 of FIG. 3B. Depot 28 may have any preselected depth d, width w, and geometrical configuration. Depth d and width w of depot 28 typically depend on the material and dimensions of implantable device 10 and the type and amount of substances deposited within depot 28 as well as on the clinical purpose and usage of implantable device 10. Depth d and width w of the individual depots 28 formed on a single implantable device 10 can vary relative to one another.

Depot 28 may be formed in a variety of selected geometrical shapes including, but not limited to, generally cylindrical shapes, generally conical shapes, generally round shapes, elongated trenches, and irregular shapes.

Composition

A composition to be applied to implantable device 10 is prepared by conventional methods wherein all components are combined and blended. More particularly, in accordance with one embodiment, a predetermined amount of a polymer is added to a predetermined amount of a solvent. The term polymer is intended to include a product of a polymerization reaction inclusive of homopolymers, copolymers, terpolymers, etc., whether natural or synthetic, including random, alternating, block, graft, crosslinked, hydrogels, blends, compositions of blends and variations thereof.

The polymer should be biocompatible, for example a polymeric material which, in the amounts employed, is non-toxic and chemically inert as well as substantially non-immunogenic and non-inflammatory. Suitable polymeric materials include, but are not limited to, bioabsorbable polymers, biomolecules, and biostable polymers. A bioabsorbable polymer breaks down in the body and is not present sufficiently long after delivery to cause an adverse local response. Bioabsorbable polymers are gradually absorbed or eliminated by the body by hydrolysis, metabolic process, bulk, or surface erosion. Examples of bioabsorbable materials include, but are not limited to, polycaprolactone (PCL), poly-D, L-lactic acid (DL-PLA), poly-LM-lactic acid (L-PLA), poly(lactide-co-glycolide), poly (hydroxybutyrate), poly(hydroxybutyrate-co-valerate), polyorthoester, polyanhydride, poly(glycolic acid), poly(glycolic acid-cotrimethylene carbonate), polyphosphoester, polyphosphoester urethane, poly (amino acids), cyanoacrylates, poly(trimethylene carbonate), poly(iminocarbonate), copoly(ether-esters), polyalkylene oxalates, polyphosphazenes, polyiminocarbonates, and aliphatic polycarbonates. Biomolecules such as heparin, fibrin, fibrinogen, cellulose, starch, and collagen are typically also suitable. A biostable polymer does not break down in the body, and thus a biostable polymer is present in the body for a substantial amount of time after delivery unless some modification is made to allow the polymer to break down. Examples of biostable polymers include, but are not limited to, PARYLENE, PARYLAST, polyurethane (for example, segmented polyurethanes such as BIOSPAN), polyethylene, polyethlyene teraphthalate, ethylene vinyl acetate, silicone, and polyethylene oxide.

The solvent can be any single solvent or a combination of solvents capable of dissolving the polymer. The particular solvent or combination of solvents selected is dependent on factors such as the material from which implantable device 10 is made and the particular polymer selected. Representative examples of suitable solvents include, but are not limited to, aliphatic hydrocarbons, aromatic hydrocarbons, alcohols, ketones, dimethyl sulfoxide (DMSO), tetrahydrofuran (THF), dihydrofuran (DHF), dimethylacetamide (DMAC), acetates and combinations thereof.

The addition of the polymer to the solvent may be conducted at ambient pressure and under anhydrous atmosphere. If necessary, gentle heating and stirring and/or mixing can be employed to effect dissolution of the polymer into the solvent, for example about 12 hours in a water bath at about 60° C.

The polymer can constitute from about 0.5% to about 20%, or more particularly from about 5% to about 10%, by weight of the total weight of the composition, and the solvent can constitute from about 80% to about 99.5%, or more particularly from about 90% to about 95%, by weight of the total weight of the composition. A specific weight ratio is dependent on factors such as the material from which implantable device 10 is made, the geometrical structure of implantable device 10 and of depots 28, the particular polymer or combination of polymers selected, the particular solvent or combination of solvents selected, the solubility of the selected polymer(s) in the selected solvent(s), and the method by which the composition will be applied to implantable device 10.

In accordance with another embodiment, sufficient amounts of a therapeutic substance or a combination of therapeutic substances are dispersed in the blended composition of the polymer and the solvent. In this embodiment, the polymer can constitute from about 0.5% to about 20% by weight of the total weight of the composition, the solvent can constitute from about 60% to about 99.4% by weight of the total weight of the composition, and the therapeutic substance can constitute from about 0.1% to about 20% by weight of the total weight of the composition. More particularly, the concentration of the therapeutic substance in the composition may be from about 1–9 times the concentration of the polymer in the composition.

In addition to the factors listed above, selection of a specific weight ratio of the polymer and the solvent in embodiments in which a therapeutic substance is employed is dependent on factors such as the type and amount of therapeutic substance employed. The particular weight percentage of a therapeutic substance mixed within the composition depends on factors such as the type of therapeutic substance selected, the solubility of the selected therapeutic substance, the duration of the release, the cumulative amount of release, and the release rate that is desired.

The therapeutic substance may be in true solution or saturated in the composition. If the therapeutic substance is not completely soluble in the composition, operations such as gentle heating, mixing, stirring, and/or agitation can be employed to effect homogeneity of the residues. However, care should be taken to ensure that the use of heat to effect dissolution does not also cause denaturation of a heat-sensitive therapeutic substance such as, but not limited to, a proteinaceous therapeutic substance.

Alternatively, the therapeutic substance may be encapsulated in a sustained delivery vehicle such as, but not limited to, a liposome or an absorbable polymeric particle. The preparation and use of such sustained delivery vehicles are well known to those of ordinary skill in the art. The sustained delivery vehicle containing the therapeutic substance is then suspended in the composition.

Inclusion of the therapeutic substance in the composition should not adversely alter the therapeutic substance's composition or characteristic. Accordingly, the particular therapeutic substance is selected for mutual compatibility with the other components of the composition.

In some embodiments, the therapeutic substance includes, but is not limited to, antineoplastic, antimitotic, antiinflammatory, antiplatelet, anticoagulant, antifibrin, antithrombin, antiproliferative, antibiotic, antioxidant, antiallergic, antiangiogenic, and angiogenic substances as well as combinations thereof. Examples of such antineoplastics and/or antimitotics include paclitaxel (e.g., TAXOL by Bristol-Myers Squibb Co., Stamford, Conn.), docetaxel (e.g., TAXOTERE from Aventis S.A., Frankfurt, Germany) methotrexate, azathioprine, vincristine, vinblastine, fluorouracil, doxorubicin hydrochloride (e.g., ADRIAMYCIN from Pharmacia & Upjohn, Peapack N.J.), and mitomycin (e.g., MUTAMYCIN from Bristol-Myers Squibb Co., Stamford, Conn.) Examples of such suitable antiinflammatories include glucocorticoids such as dexamethasone, methylprednisolone, hydrocortisone and betamethasone, superpotent glucocorticoids such as clobustasol, halobetasol, and diflucortolone, and non-steroidal antiinflammatories such as aspirin, indomethacin and ibuprofen. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.) Examples of such cytostatic or antiproliferative agents include actinomycin D as well as derivatives and analogs thereof (manufactured by Sigma-Aldrich, Milwaukee, Wis.; or COSMEGEN available from Merck & Co., Inc., Whitehouse Station, N.J.), angiopeptin, angiotensin converting enzyme inhibitors such as captopril (e.g., CAPOTEN and CAPOZIDE from Bristol-Myers Squibb Co., Stamford, Conn.), cilazapril or lisinopril (e.g., PRINIVIL and PRINZIDE from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example-of an antiallergic agent is permirolast potassium. Examples of antiangiogenic agents include thalidomide and angiostatin. Examples of angiogenic agents include vascular endothelial cell growth factor (VEGF) and fibroblast growth factor (FGF). Examples of arteriogenic agents include histimine, MCP-1, lipo-polysaccharide, and β-FGF. Other therapeutic substances or agents that may be used include alpha-interferon, genetically engineered epithelial cells, and dexamethasone. While the preventative and treatment properties of the foregoing therapeutic substances or agents are well-known to those having ordinary skill in the art, the substances or agents are provided by way of example and are not meant to be limiting. Other therapeutic substances are equally applicable for use with the disclosed methods and compositions.

In other embodiments, the therapeutic substance may be a radioactive isotope. Examples of radioactive isotopes include, but are not limited to, phosphorus ($p^{32}$), palladium ($Pd^{103}$), cesium ($Cs^{131}$), and iodine ($I^{125}$).

In still other embodiments, the therapeutic substance is a nucleic acid or a protein. Examples of such nucleic acids include phosphorodiamidate morpholino oligomers (PMO), cyclic-3'-5'-adenosine monophosphate (8-C1-cAMP), Antisense oligonucleotides, and various nucleic acids encoding for growth factors such as vascular endothelial cell growth factor (VEGF) and fibroblast growth factor (FGF). Examples of proteins include growth factors such as VEGF and FGF.

In addition, the composition may include more than one therapeutic substance. In such embodiments, the number, type, and ratio of therapeutic substances within the composition are treatment-specific. However, the substances within the composition should be mutually compatible, such that the characteristics, effectiveness, and physical structure of the substances are not adversely altered. Therapeutic substances that are not mutually compatible should be isolated from one another within the composition by, for example, encapsulating one or both of the therapeutic substances within separate sustained delivery vehicles.

In still other embodiments, the composition may include a radiopaque substance. Such substances help to facilitate implantable device usage in radiotherapeutic procedures. A example of a radiopaque substance is gold.

As described further below, the composition is applied to implantable device 10 to form a coating thereon.

Coating the Implantable Device
a. Application of the Composition

Prior to applying the composition to implantable device 10, outer surface 20 and depots 28 should be clean and free from contaminants that may be introduced during manufacturing. However, outer surface 20 and depots 28 of implantable device 10 require no particular pretreatment to retain the applied coating.

Referring again to FIG. 1, the above-described composition is applied to implantable device 10 at a first gas pressure in act 101 of method 100. Typically, the gas pressure at which the composition is applied to implantable device 10 is ambient pressure. However, any gas pressure at which the composition may be properly applied to implantable device 10 is suitable for use with the embodiments of the present invention. The composition may be applied to implantable device 10 by any conventional method, such as by spraying the composition onto implantable device 10 or immersing implantable device 10 in the composition. Variations of spray and immersion techniques are also suitable methods of applying the composition to implantable device 10. In one such variation, the composition may be applied by first spraying or immersing implantable device 10 as described above. The composition-coated implantable device 10 is then centrifuged. The rotation of implantable device 10 creates a centrifugal force upon the composition applied to implantable device 10. This centrifugal force causes excess accumulations of the composition to be more evenly redistributed over implantable device 10 and thus provides a more even, uniform coating of the composition on implantable device 10. The rotational speed during centrifugation can be varied. Higher RPM values may provide improved uniformity and a reduction in defects. However, lower RPM values improve the total loading of the composition onto implantable device 10. Increasing the total centrifuigation time may also improve the uniformity and reduce defects in the coating of the composition on implantable device 10.

Figure 4A:
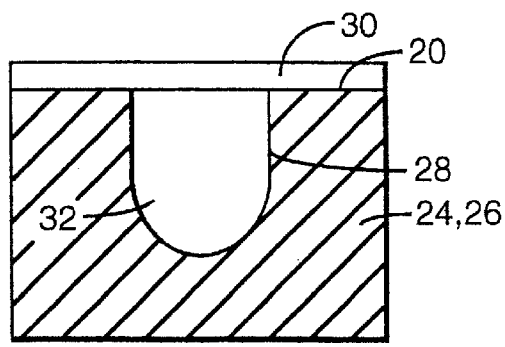
FIGS. 4A, 4B, 4C, and 4D illustrate the stent of FIG. 3C after the composition has been applied.
Figure 4B:
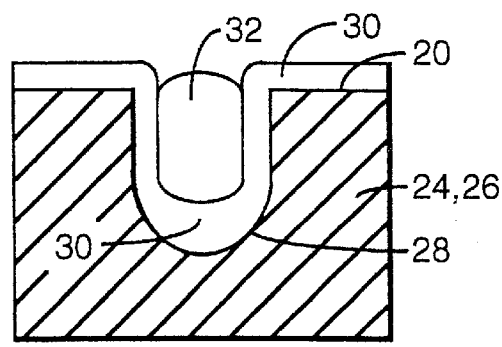
Figure 4C:
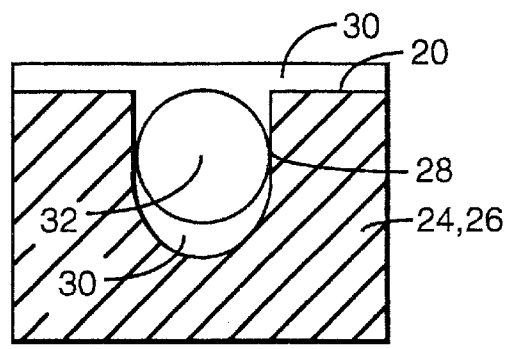
Figure 4D:
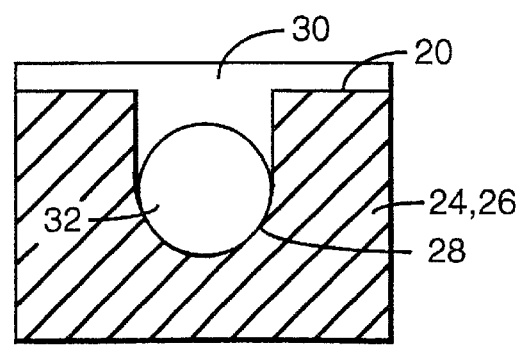

As mentioned above, and as shown in FIGS. 4A–4D, undesirable air pockets 32 form in depots 28 when conventional coating methods are used. The air pockets 32 prevent composition 30 from completely filling depots 28. For example, FIG. 4A depicts an embodiment in which composition 30 is deposited solely on outer surface 20. Depot 28 contains an air pocket 32 rather than composition 30. Alternatively, some amount of composition 30 may enter depot 28 such that depot 28 is from about 0.1% to about 50% filled with composition 30. The portion of depot 28 not filled with composition 30 typically contains an air pocket 32. Air pocket 32 within depot 28 may form above, between, or below areas containing composition 30, as depicted in FIGS. 4B, 4C, and 4D, respectively. The amount of composition 30 that enters depot 28, if any, depends, in part, on the geometry of depot 28 and the surface tension of composition 30.

b. Application of an Increased Gas Pressure

Figure 5:
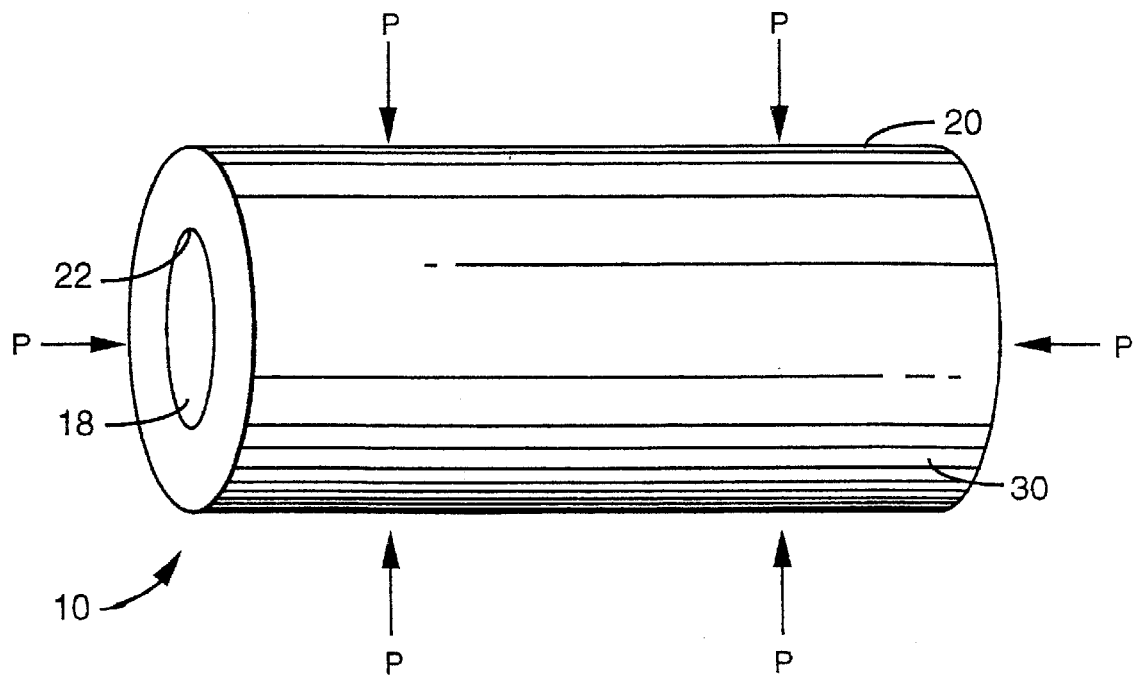
FIG. 5 illustrates the application of an increased gas pressure to the implantable device of FIG. 2A following application of the composition.

As depicted in FIGS. 1 and 5, an increased gas pressure P is uniformly applied to the composition 30-coated implantable device 10 in act 102. Gas pressure P is any gas pressure greater than the gas pressure at which act 101 is performed as described above. Gas pressure P may be greater than atmospheric pressure. By way of example and not limitation, gas pressure P ranging from about 29.4 PSI (203 kPa) to about 58.8 PSI (405 kPa) may be applied to implantable device 10 from all directions for a duration ranging from about 0.5 minute to about 20 minutes.

The actual gas pressure P selected depends, at least in part, on the viscosity of composition 30. Compositions 30 having higher viscosities, e.g., 20% polymer by weight, typically require using higher gas pressures, e.g., 58.8 PSI (405 kPa), while compositions 30 having lower viscosities, e.g., 0.5% polymer by weight, typically require using lower gas pressures, e.g., 29.4 PSI (203 kPa). Regardless of the viscosity of composition 30, the gas pressure P applied should not be so high as to cause phase separation or precipitation.

The duration for which gas pressure P is applied depends, in part, on the viscosity of composition 30 and the actual gas pressure P applied. Compositions 30 having higher viscosities, e.g., 20% polymer by weight, typically require that gas pressure P be applied for a longer duration, e.g., 10 minutes, while compositions 30 having lower viscosities, e.g., 0.5% polymer by weight, typically require that gas pressure P be applied for a shorter duration, e.g., 0.5 minute. Similarly, higher gas pressures, e.g., 58.8 PSI (405 kPa), typically are applied for a shorter duration, e.g., 5 minutes, while lower gas pressures, e.g., 29.4 PSI, typically are applied for a longer duration, e.g., 20 minutes.

The gas utilized in the application of gas pressure P may be air, carbon dioxide, nitrogen, or any other gas suitable for use with implantable device 10 and composition 30. The source of gas pressure P may be any suitable source capable of applying the appropriate amount of gas pressure P for the appropriate duration to implantable device 10 uniformly from all directions as discussed above. One example of a suitable source of gas pressure P is a sealable pressure chamber into which the composition 30-coated implantable device 10 may be placed in entirety.

Figure 6A:
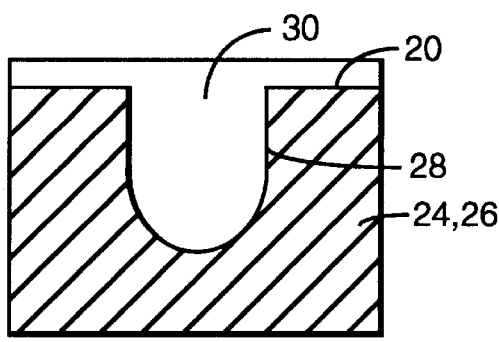
FIGS. 6A, 6B, and 6C illustrate the composition-coated stent of FIG. 4A after an increased gas pressure has been applied such that the composition is driven into the depot.
Figure 6B:
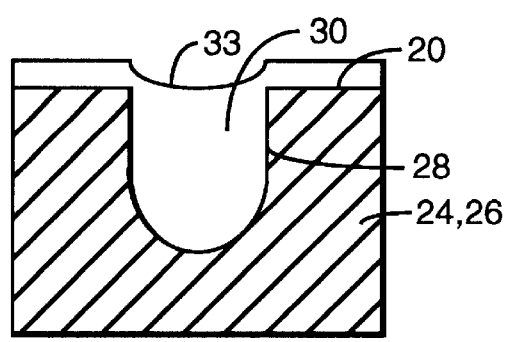
Figure 6C:
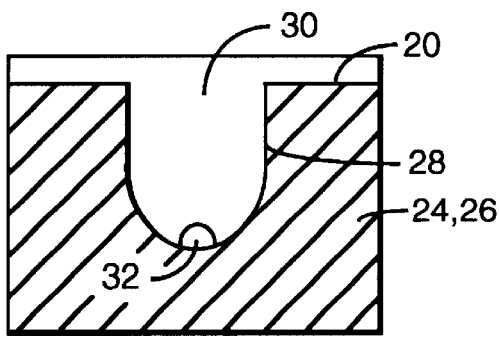

Gas pressure P drives composition 30 into depots 28 of implantable device 10. As a result, composition 30 may completely displace air pocket 32 within depot 28 such that depot 28 becomes completely filled with composition 30, as depicted in FIGS. 6A and 6B. In other embodiments, composition 30 may partially displace air pocket 32, or alternatively compress air pocket 32 such that air pocket 32 occupies a smaller portion of depot 28 after the pressure treatment than before the pressure treatment, as depicted in FIG. 6C.

Composition 30 may not be of uniform thickness along outer surface 20 following the pressure treatment in act 102. For example, as shown in FIG. 6B, a dimple 33 may form in composition 30 above depot 28.

c. Removal of the Solvent from the Composition

Figure 7A:
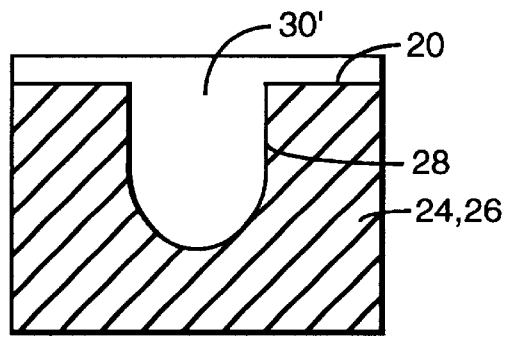
FIGS. 7A, 7B, and 7C illustrate the stents of FIGS. 6A, 6B, and 6C, respectively, after the solvent has been removed from the composition to form a coating.
Figure 7B:
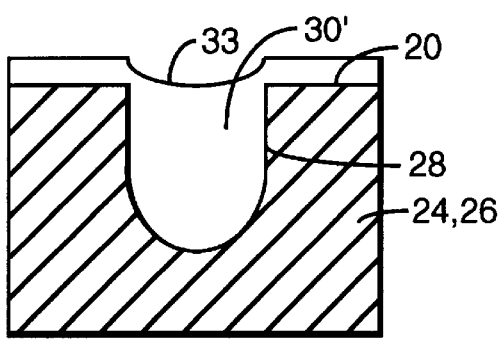
Figure 7C:
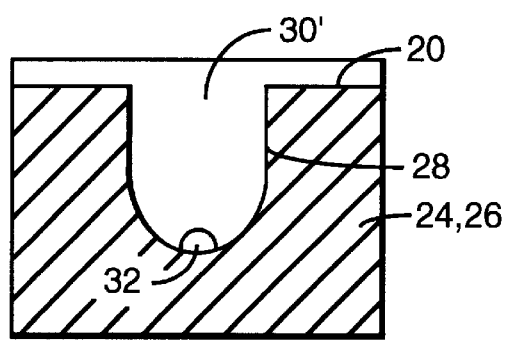

The solvent is removed from composition 30 on implantable device 10 in act 103. The solvent may be removed using techniques such as, but not limited to, evaporation at ambient pressure and room temperature in an anhydrous atmosphere for 48 hours, or exposure to mild heat, e.g., 60–65° C., under vacuum conditions. In embodiments where implantable device 10 is made of a bioabsorbable polymer, the solvent should be removed relatively quickly to avoid prolonged exposure and thereby ensure the mechanical integrity of the implantable device 10. Upon removal of essentially all of the solvent, a stable polymeric coating 30' remains on implantable device 10, including on outer surface 20 and within depots 28, as depicted in FIGS. 7A, 7B, and 7C.

In some embodiments, application of increased gas pressure P in act 102 continues during the removal of solvent from composition 30 in act 103. In such embodiments, components of composition 30 other than the solvent, i.e., polymeric material and any therapeutic substances, will adhere to the interior surface of depot 28. Thus, when the gas pressure upon implantable device 10 is reduced following the removal of solvent from composition 30, any air pocket 32 remaining trapped within depot 28 will not expand, but rather, will retain its reduced size.

d. Optional Removal of the Composition or the Coating from Outer Surface

Figure 8A:
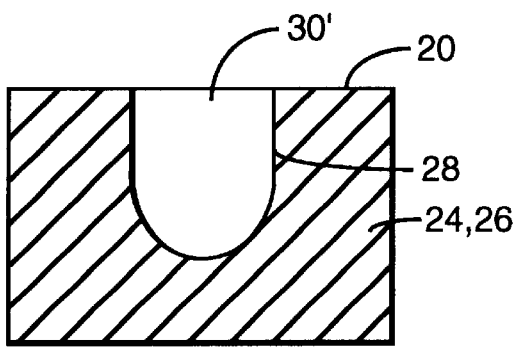
FIG. 8A illustrates the stent of FIG. 6A after surplus composition or coating has been removed from areas other than within the depot.
Figure 8B:
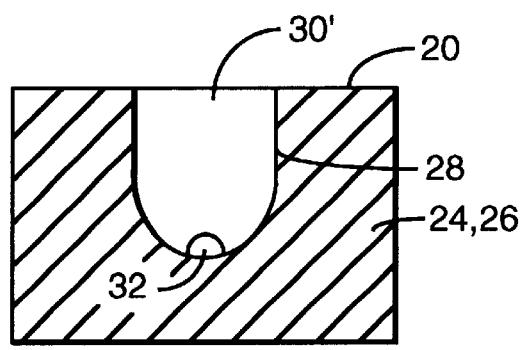
FIG. 8B illustrates the stent of FIG. 6C after surplus composition or coating has been removed from areas other than within the depot.

It may be desirable to treat implantable device 10 so that coating 30' is present only within depots 28, and not on outer surface 20 around depots 28, as depicted in FIGS. 8A and 8B. To obtain such embodiments, undesirable portions of composition 30 may be removed prior to the removal of the solvent. Alternatively, undesired portions of coating 30' may be removed after coating 30' is formed by removal of the solvent.

Conventional techniques, such as, but not limited to, scraping, squeegeeing, washing, blowing, or spinning may be used to remove the undesired portions of composition 30 or coating 30'. The scraping method involves the mechanical stripping of composition 30 or coating 30' from outer surface 20 using, for example, a brush. The squeegeeing method involves passing implantable device 10 through an opening in a sponge filled with cleaning solution containing liquids such as, but not limited to, water, ethanol, DMSO, or hexane. The washing method may involve soaking implantable device 10 in a cleaning solution containing liquids such as, but not limited to, water, ethanol, DMSO, or hexane. Alternatively, the washing method may involve rinsing implantable device 10 having coating 30' thereon with the same solvent used in composition 30. The washing methods may or may not include sonication. The blowing method may include passing air pressure over outer surface 20 having composition 30 thereon such that compostion 30 or coating 30' is blown offouter surface 20. The spinning methods may include spinning implantable device 10, such as by centrifugation, so as to drive composition 30 off outer surface 20. Of course, care should be taken during the removal of composition 30 or coating 30' from outer surface 20 such that composition 30 or coating 30' is not also removed from within depot 28.

e. Optional Use of Topcoats

Figure 9A:
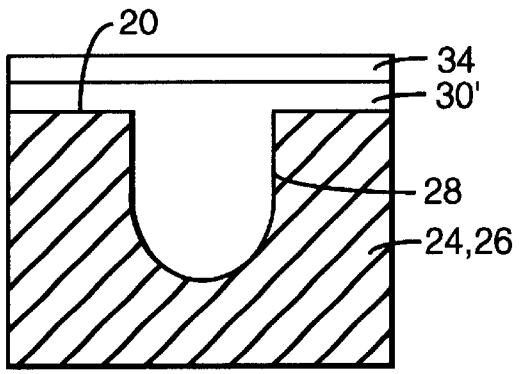
FIG. 9A illustrates the stent of FIG. 7A after a topcoat has been applied over the coated depot and along the coated outer surface.
Figure 9B:
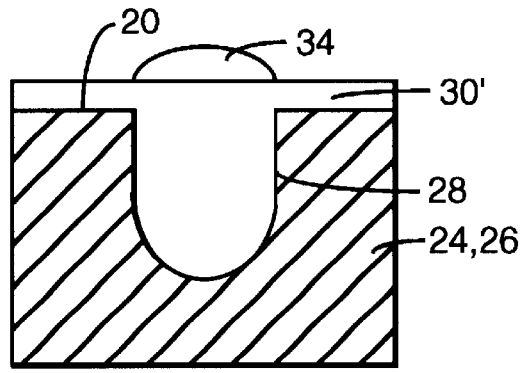
FIG. 9B illustrates the stent of FIG. 7A after a topcoat has been applied over the coated depot.
Figure 9C:
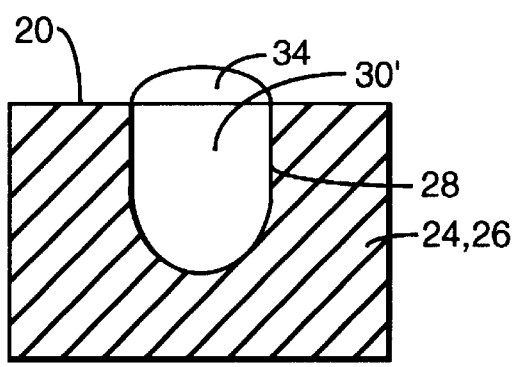
FIG. 9C illustrates the stent of FIG. 8A after a topcoat has been applied over the coated depot.

In some embodiments, a polymeric topcoat 34, with or without a therapeutic substance therein, is deposited over coating 30' on implantable device 10 in act 106, as depicted in FIGS. 9A, 9B, and 9C. FIG. 9A illustrates an embodiment in which topcoat 34 is applied over coated outer surface 20 as well as above coated depot 28. In alternative embodiments depicted in FIGS. 9B and 9C, topcoat 34 is applied solely above coated depot 28. Polymeric topcoat 34 can be applied in act 106 by any conventional method, such as the immersion or spray techniques described above with reference to the application of composition 30.

Polymeric topcoat 34 will typically reduce the rate of release of a substance or substances from implantable device 10. The polymers that were listed above with reference to polymers suitable for inclusion in composition 30 are equally applicable here. By way of example, and not limitation, the polymeric topcoat 34 can have a thickness of about 0.25 microns to about 1.5 microns. Typically, topcoat 34 can have a thickness of about 1 micron. It will be appreciated by one of ordinary skill in the art that the thickness of the polymeric topcoat 42 is based on factors such as the type of procedure for which implantable device 10 is employed and the rate of release that is desired.

In act 107 of method 100, any solvent within topcoat 34 is removed following application to implantable device 10. Removal of the solvent from topcoat 34 may be accomplished using conventional methods known to one of ordinary skill in the art, such as those listed above with reference to the removal of solvent from composition 30, which are equally applicable here.

Methods of Use

As mentioned above, implantable devices that may be treated according to the methods of the present invention include stents and grafts, among other possibilities. An implanted stent or graft having the above-described coating is useful for treating occluded regions of blood vessels caused by thrombosis and/or restenosis, among other possible uses.

Stents may be placed in a wide array of blood vessels, both arteries and veins. Briefly, an angiography is first performed to determine the appropriate positioning for stent therapy. Angiography is typically accomplished by using a catheter to inject a radiopaque contrasting agent into an artery or vein as an X-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein and advanced into the appropriate blood vessel by steering the catheter through the vascular system under fluoroscopic guidance. A stent having the above described covering may then be expanded at the desired area of treatment. A post-insertion angiogram may also be utilized to confirm appropriate positioning.

Vascular grafts may be used to replace, bypass, or reinforce diseased or damaged sections of a vein or artery. The general procedure for implantation includes the step of pre-clotting, wherein the graft is immersed in the blood of the patient and allowed to stand for a period of time sufficient for clotting to ensue. After pre-clotting, hemorrhaging is less likely to occur when the graft is implanted, and thus the growth of tissue is not impeded. Grafts may be placed either through invasive surgery or non-invasively through percutaneous endoluminal transport. Percutaneous delivery of a graft avoids the complications and risks of surgery. The graft may be attached to the vessel at each end of the diseased region, thus bypassing the diseased region. Alternatively, the diseased region may be removed and replaced by the graft.

While particular embodiments and applications of the present invention have been shown and described, those of ordinary skill in the art will appreciate that changes and modifications can be made without departing from this invention in its broader aspects. Therefore, the appended claims are to encompass within their scope all such changes and modifications as fall within the true spirit and scope of this invention.

We claim:

1. A method of depositing a polymer into a plurality of depots formed in an outer surface of a stent comprising:

applying a composition comprising a polymer and a solvent to said plurality of depots, wherein said act of applying said composition is performed at a first gas pressure;

applying a second gas pressure to said composition in said depots, wherein said second gas pressure is greater than said first gas pressure and less than the pressure which causes phase separation or precipitation of said polymer in said composition, and wherein said second gas pressure is sufficient to remove air pockets from said composition in said depots; and removing said solvent from said composition, wherein a polymeric deposit is formed substantially free from air pockets in said depots of said stent.

2. The method of claim 1, wherein said composition comprises a therapeutic substance.

3. The method of claim 2, wherein said therapeutic substance is selected from a group consisting of antineoplastic, antimitotic, antiinflammatory, antiplatelet, anticoagulant, antifibrin, antithrombin, antiproliferative, antibiotic, antioxidant, and antiallergic substances and combinations thereof.

4. The method of claim 2, wherein said therapeutic substance is selected from a group consisting of radioisotopes and radiopaque substances.

5. The method of claim 1, wherein said second gas pressure is a gauge pressure of about 29.4 PSI to about 58.8 PSI.

6. The method of claim 1, wherein said second gas pressure is greater than atmospheric pressure.

7. The method of claim 1, wherein the act of applying said composition to said depots comprises applying said composition to said stent and allowing said composition to penetrate into said depots.

8. The method of claim 7, further comprising removing said composition from portions of said outer surface of said stent outside of said depots.

9. The method of claim 1, further comprising applying a polymeric topcoat at least over said depots.

10. The method of claim 1, wherein said second pressure is applied for a duration of about 0.5 minutes to about 20 minutes.

11. The method of claim 1, wherein said first pressure is at least atmospheric pressure.

12. A method of loading a substance into a plurality of depots of a stent comprising:

applying a composition including a polymer and a solvent to said depots, said composition having a polymer content between about 0.5% and 20% by weight, and wherein said act of applying said composition is performed at a first gas pressure of at least atmospheric pressure;

placing the stent in a sealable pressure chamber; and applying a second gas pressure to said composition, said second gas pressure being a gauge pressure of about 29.4 PSI to about 58.8 PSI, wherein said second gas pressure is greater than said first gas pressure and less than the pressure which causes phase separation or precipitation of said polymer in said composition and is sufficient to remove air pockets from said composition in said depots.

13. The method of claim 12, wherein said polymer is selected from a group consisting of bioabsorbable polymers, biomolecules, and biostable polymers.

14. The method of claim 13, wherein said composition further comprises a therapeutic substance.

15. The method of claim 14, wherein said therapeutic substance is selected from a group consisting of antineoplastic, antimitotic, antiinflammatory, antiplatelet, anticoagulant, antifibrin, antithrombin, antiproliferative, antibiotic, antioxidant, and antiallergic substances and combinations thereof.

16. The method of claim 14, wherein said therapeutic substance is selected from a group consisting of radioisotopes.

17. The method of claim 14, further comprising applying a polymeric topcoat over said depots.

18. The method of claim 12, further comprising removing said solvent from said composition.

19. The method of claim 12, wherein said second pressure is applied for a duration of about 0.5 minutes to about 20 minutes.

20. A method of depositing a substance in depots of an implantable device, comprising:
    applying said substance in a liquid carrier to said device wherein said substance and said liquid carrier are allowed to penetrate into said depots;
    placing said device in a sealable pressure chamber;
    applying a first pressure greater than atmospheric pressure to said device so as to significantly reduce the size of the air pockets in said depots;
    removing said liquid carrier from said device while applying a second pressure greater than atmospheric pressure to maintain the reduced size of the air pockets; and
    applying a third pressure to said device subsequent to said removal of said liquid carrier wherein said third pressure is less than said first and second pressures.

21. The method of claim 20, wherein said substance is a polymer.

22. The method of claim 20, wherein said substance is a drug.

23. The method of claim 20, wherein said substance is a mixture of a polymer and a drug.

24. The method of claim 20, wherein said first pressure does not cause phase separation or precipitation of said substance in said liquid carrier.

25. The method of claim 20, wherein said first pressure is equal to said second pressure.

26. The method of claim 20, wherein said application of said substance is performed while said device is in said pressure chamber.

27. A method of depositing a substance in depots of a stent, comprising:
    applying a composition including a substance to said stent wherein said composition penetrates into said depots of said stent; and
    applying a pressure to said composition to essentially remove air pockets or reduce the size of air pockets from said composition in said depots, wherein said pressure does not cause phase separation or precipitation of said substance in said composition in said depots of said stent.

28. The method of claim 27, wherein said substance includes a drug.

29. The method of claim 27, wherein said substance includes a polymer.

30. The method of claim 27, wherein said substance is a mixture of a polymer and a drug.

31. The method of claim 27, wherein said composition includes a solvent and wherein said method additionally comprises allowing said solvent to evaporate.

32. A method of depositing a substance in depots of an implantable device, comprising:
    applying said substance in a liquid carrier to said device wherein said substance and said liquid carrier are allowed to penetrate into said depots;
    placing said device in a sealable pressure chamber;
    applying a first pressure to said device so as to significantly eliminate or reduce the size of the air pockets in said depots;
    removing said liquid carrier from said device; and
    applying a second pressure to said device subsequent to said removal of said liquid carrier wherein said second pressure is less than said first pressure.

* * * * *